United States Patent [19]

Hatanaka et al.

[11] Patent Number: 5,008,405
[45] Date of Patent: Apr. 16, 1991

[54] SELECTIVE ETHERIFICATION

[75] Inventors: Chitoshi Hatanaka, Nagaokakyo; Satoru Oi, Nara, both of Japan

[73] Assignee: Takeda Chemical Industries, Ltd., Osaka, Japan

[21] Appl. No.: 467,419

[22] Filed: Jan. 19, 1990

[30] Foreign Application Priority Data

Jan. 21, 1989 [JP] Japan .................................. 1-12755

[51] Int. Cl.$^5$ .......................................... C07D 307/62
[52] U.S. Cl. ..................................... 549/315; 549/264
[58] Field of Search ................................ 549/315, 264

[56]   References Cited

U.S. PATENT DOCUMENTS 4,552,888 11/1985 Koppel et al. ...................... 549/315

FOREIGN PATENT DOCUMENTS 146121 6/1985 European Pat. Off. ............ 549/315
202589 11/1986 European Pat. Off. ............ 549/315
259707 3/1988 European Pat. Off. ............ 549/315

OTHER PUBLICATIONS

Kaneyoshi Kato et al., "Studies on Scavengers of Active Oxygen Species, 1. Synthesis and Biological Activity of 2-O-Alkyl-Ascorbic Acids," J. Med. Chem. 1988, 31, pp. 793-798.
P. A. Seib, et al., *J. Chem. Soc., Perkin I,* "Synthesis and Stability of L-Ascorbate 2-Sulphate," pp. 1220-1224 (1974).
C. H. Lee, et al., *Carbohydrate Research,* "Chemical Synthesis of Several Phosphoric Esters of L-Ascorbic Acid," 67, pp. 127-138, (1978).
J. Jernow, et al., *Tetrahedron,* "Structural Determination of Ascorbic Acid 2-O-Phosphate via Acid Hydrolysis . . . ," 35 (12), pp. 1483-1486 (1979).

*Primary Examiner*—Richard L. Raymond
*Assistant Examiner*—Mark W. Russell
*Attorney, Agent, or Firm*—Wegner, Cantor, Mueller & Player

[57]   ABSTRACT

There is disclosed an improved process for substitution of the hydroxy group at 2-position of an ascorbic acid derivative according to the following reaction scheme:

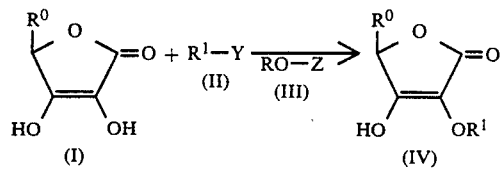

wherein $R^0$ is hydrogen, alkyl having 1 to 6 carbon atoms, phenyl or a group of the formula

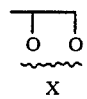

(wherein X is two hydrogen atoms, or acetal or ketal residue); $R^1$ is an alkyl or alkenyl group having up to 22 carbon atoms which may be substituted with phenyl or alkoxy having 1 to 22 carbon atoms; Y is halogen or optionally substituted sulfonyloxy; R is hydrogen, or primary, secondary or tertiary alkyl having 1 to 10 carbon atoms; and Z is an alkali metal or an alkali earth metal. There is also disclosed hydrolysis of the following scheme:

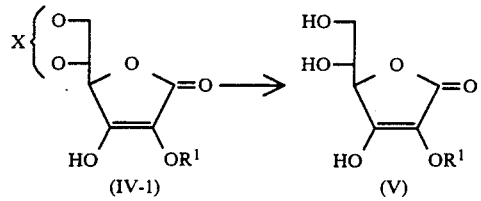

wherein $R^1$ is as defined above; and X is acetal or ketal residue.

10 Claims, No Drawings

SELECTIVE ETHERIFICATION

FIELD OF THE INVENTION

The present invention relates to a process for producing ascorbic acid derivatives which are useful as antioxidants for food and agents for ameliorating and preventing functional disorders of circulatory and digestive systems.

BACKGROUND OF THE INVENTION

As processes for producing an ascorbic acid derivative wherein the hydroxy group at 2-position is substituted, there have been known, for example, the following processes:

(1) A process wherein, after protecting the hydroxy groups at the 3-, 5- and 6-positions of ascorbic acid, the hydroxy group at the 2-position is substituted and, then, hydrolyzed and/or reduced to obtain the objective ascorbic acid derivative (see, EP-A-O 146 121 and EP-A-O 202 589);

(2) A process wherein, after protecting the hydroxy group at 6-position of ascorbic acid, the hydroxy group at 2-position is substituted, or both hydroxy groups at 2- and 6-positions are substituted, simultaneously [see, Tanaka et al., Yakugaku Zasshi, 86, p. 376 (1966)];

(3) A process wherein, after protecting the hydroxy groups at the 5- and 6-positions of ascorbic acid with an isopropylidene group, the hydroxy group at 2-position is phosphorylated and, then, the isopropylidene groups are removed [Chen H. Lee et al., Carbohydrate Research, 67, 127-138 (1978)];

(4) A process wherein, after protecting the hydroxy groups at the 5- and 6-position of ascorbic acid with isopropylidene, the hydroxy group at 2-position is substituted with sulfonic group and, then, the resultant is subjected to acid hydrolysis to remove the isopropylidene groups [see, Paul A. Seib et al., J. Chem, Soc., Perkin Trans. 1, 1220 (1974)]; and (5) A process wherein, after protecting the hydroxy group at the 3-position of 5,6-O-isopropylidene ascorbic acid, the hydroxy group at the 2-position is alkylated with an alkyl halide and, then, the resultant is deprotected [see, Kato et al., J. Med. Chem., 31, 793-798 (1988)].

In order to introduce an alkyl group into the 2-position of ascorbic acid to obtain a 2-O-alkylascorbic acid derivative, as a general process, there has been employed a process wherein both the hydroxy groups at 5- and 6-positions are firstly protected to increase solubility in an organic solvent and, then, the hydroxy group at the 3-position which is more acidic and reactive than the hydroxy group at the 2-position is protected, followed by introduction of an alkyl group into the hydroxy group at the 2-position. However, from the industrial point of view, the above process is economically and operationally disadvantageous because the residues which do not constitute the structure of the objective compound are introduced as the protective groups. Further, alkylation at the 2-position with an alkyl halide is accompanied with a side reaction wherein the hydroxy group at the 3-position is also partly alkylated, even if it is protected, which results in insufficient yield.

OBJECTS OF THE INVENTION

The main object of the present invention is to provide an industrially advantageous process for producing ascorbic acid derivatives by direct alkylation or alkenylation of the hydroxy group at the 2-position of ascorbic acid or 5,6-protected ascorbic acid.

This object as well as other objects and advantages of the present invention will become apparent to those skilled in the art from the following description.

SUMMARY OF THE INVENTION

According to the present invention, there is provided a process for producing a compound of the formula (IV):

wherein $R^0$ is hydrogen, alkyl having 1 to 6 carbon atoms, phenyl or a group of the formula

(wherein X represents two hydrogen atoms, or an acetal or ketal residue); and $R^1$ is an alkyl or alkenyl group having up to 22 carbon atoms which may be substituted with phenyl or alkoxy having 1 to 22 carbon atoms, which comprises reacting a compound of the formula (I):

wherein $R^0$ is as defined above, with a compound of the formula (II):

$$R^1-Y \qquad (II)$$

wherein $R^1$ is as defined above; and Y is halogen or optionally substituted sulfonyloxy, in the presence of a compound of the formula (III):

$$RO-Z \qquad (III)$$

wherein R is hydrogen, or primary, secondary or tertiary alkyl having 1 to 10 carbon atoms; and Z is an alkali metal or an alkaline earth metal. The present invention also provides a process for producing a compound of the formula (V):

wherein $R^1$ is as defined above, which comprises hydrolyzing the compound of the above formula (IV) wherein $R^0$ is of the formula

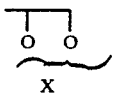

(wherein X is acetal or ketal residue).

DETAILED DESCRIPTION OF THE INVENTION

In the above formulas, the alkyl having 1 to 6 carbon atoms represented by $R^0$ can be either straight or branched-chain alkyl. Examples thereof include methyl, ethyl, n-propyl, isopropyl, n-butyl, isobutyl, n-pentyl, n-hexyl and the like.

The alkyl moiety of the alkyl group having up to 22 carbon atoms which may be substituted with phenyl or alkoxy having 1 to 22 carbon atoms represented by $R^1$ can be either straight or branched-chain alkyl having 1 to 22 carbon atoms. Examples thereof include methyl, ethyl, n-propyl, isopropyl, n-butyl, isobutyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-heneicosyl, n-docosyl and the like.

Preferably, the alkyl has 9 to 20 carbon atoms. Particularly, straight-chain alkyl having 14 to 20 carbon atoms is preferred.

The alkenyl moiety of the alkenyl group having up to 22 carbon atoms which may be substituted with phenyl or alkoxy having 1 to 22 carbon atoms represented by $R^1$ can be either straight or branched-chain alkenyl. Examples thereof include vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl and the like.

The above alkoxy having 1 to 22 carbon atoms can be either straight or branched-chain alkoxy. Examples thereof include methoxy, ethoxy, n-propoxy, isopropoxy, n-butoxy, isobutoxy, n-pentyloxy, n-hexyloxy, n-decyloxy, n-tetradecyloxy, n-octadecyloxy and the like.

In the above formulas, the acetal residue represented by X includes, for example, that represented by the formula:

wherein $R^2$ is alkyl having 1 to 3 carbon atoms, phenyl or p-methoxyphenyl. The ketal residue includes, for example, that represented by the formula:

wherein $R^3$ and $R^4$ are the same or different and alkyl having 1 to 3 carbon atoms, or $R^3$ together with $R^4$ forms $-(CH_2)_a-$ (in which a is 4 or 5).

The above alkyl having 1 to 3 carbon atoms includes, for example, methyl, ethyl, n-propyl, isopropyl.

In the above formulas, the halogen represented by Y includes chlorine, bromine and iodine. Among them, iodine is preferred.

The substituent of the optionally substituted sulfonyloxy group represented by Y includes alkyl having 1 to 6 carbon atoms (for example, those illustrated with respect to the $R^0$ group) and aryl (e.g., phenyl, p-tolyl, p-nitrophenyl, p-chlorophenyl, etc.). Examples of the optionally substituted sulfonyloxy group include sulfonyloxy, alkyl sulfonyloxy such as methylsulfonyloxy, ethylsulfonyloxy, propylsulfonyloxy and the like, and aryl sulfonyloxy such as phenylsulfonyloxy, p-tolylsulfonyloxy, p-nitrophenylsulfonyloxy, p-chlorophenylsulfonyloxy and the like. Among them, the aryl sulfonyloxy group is particularly preferred.

In the above formulas, the primary, secondary or tertiary alkyl having 1 to 10 carbon atoms represented by R includes primary alkyl having 1 to 10 carbon atoms (e.g., methyl, ethyl, propyl, butyl, etc.), secondary alkyl having 3 to 10 carbon atoms (e.g., isopropyl, isobutyl, etc.) and tertiary alkyl having 4 to 10 carbon atoms (e.g., tertiary butyl, tertiary amyl, etc.).

The alkali metal of Z includes lithium (Li), sodium (Na), potassium (K) and the like, and the alkaline earth metal includes calcium (Ca), magnesium (Mg) and the like. Among them, the alkali metal is preferred. Instead of the alkoxide of the formula (III), a simple substance of the metal represented by Z or a hydride of Z can be used without any trouble because it is converted into RO-Z in a reaction system.

In the present invention, preferably, the reaction is carried out by using a primary, secondary or tertiary alcohol as a reaction solvent. Examples thereof include primary alcohols such as methyl alcohol, ethyl alcohol, n-propyl alcohol, n-butyl alcohol and the like, secondary alcohols such as isopropyl alcohol, isobutyl alcohol and the like, and tertiary alcohols such as t-butyl alcohol, t-amyl alcohol and the like. These primary, secondary and tertiary alcohols can be used alone or in combination thereof. Other solvents can be used together with the above primary, secondary or tertiary alcohol. Examples thereof include dioxane, tetrahydrofuran, ethylene glycol dimethyl ether, acetonitrile, toluene, dimethylformamide, dimethyl sulfoxide and the like. They can be appropriately mixed with the alcohol by taking into consideration of solubility of the compounds (I) and (II) and the like.

In the present invention, preferably, the compound (II) is used in an amount of 0.5 to 3.0 molar equivalent, particularly, 0.8 to 2.0 molar equivalent based on the compound (I).

Preferably, the amount of the compound (III) is used in an amount of 1.5 to 3.0 molar equivalent, particularly, 1.8 to 2.2 molar equivalent based on the compound (I).

The preferred reaction temperature of the reaction of the compounds (I) and (II) is generally in the range of from 10° C. to the boiling point of the reaction solvent. Particularly, the reaction is suitably carried out at 40° to 80° C.

The reaction time varies depending upon reaction conditions such as reaction temperature and the like. Generally, however, the reaction time is suitably 1 to 4 hours, when the reaction is carried out at 40° to 80° C.

In order to let the reaction proceed smoothly, the reaction is preferably carried out in the presence of an inert gas (e.g., nitrogen gas, helium gas, argon gas, etc.).

Hereinafter, the hydrolysis of the compounds (IV-1) [the compound of the formula (IV) wherein $R^0$ is represented by the formula

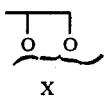

(wherein X is acetal or ketal residue)] is explained.

Preferably, after 2-alkylation, the reaction mixture is subjected to hydrolysis, if necessary with addition of water, in the presence of an acid catalyst such as hydrochloric acid, sulfuric acid, phosphoric acid, acetic acid, p-toluenesulfonic acid, methanesulfonic acid, camphorsulfonic acid, a cation exchange resin or the like at about 10° and 80° C. for about 1 to 2 hours.

Alternatively, the 2-alkylated compound is separated from the reaction mixture of 2-alkylation and then hydrolyzed. In this case, the reaction is preferably carried out in water or an organic solvent such as methanol, ethanol, dioxane, tetrahydrofuran dimethylformamide, dichloroethane or a water-containing solvent of these organic solvents in the presence of the above acid catalyst at about 10° to 80° C. for about 1 to 2 hours.

The ascorbic acid derivatives (IV) and (V) thus produced can be isolated and collected using known separation and purification means (e.g., column chromatography using silica gel, polystyrene resin, activated carbon, etc., extraction, recrystallization and the like).

The following examples and reference examples further illustrate the present invention in detail but are not to be construed to limit the scope thereof.

EXAMPLE 1

5,6-O,O-Isopropylidene-L-ascorbic acid (14 g, 0.065 mol) was added to a mixture of methanol (200 ml) and sodium methoxide (25 g, 28% (w/w) methanol solution, 0.13 mol) in a stream of nitrogen and dissolved by heating. Then, octadecyl benzenesulfonate (26.7 g, 0.065 mol) was added thereto. The mixture was stirred at about 60° C. for 2.5 hours and 2 N hydrochloric acid (60 ml) was added to the reaction mixture. The mixture was stirred under reflux for one hour. Then, water (300 ml) was added and the mixture was cooled to 20° to 25° C. The crystals precipitated were collected by filtration, dried and recrystallized from ethyl acetate to obtain 11.7 g of 2-O-octadecyl-L-ascorbic acid (yield: 42%).

Melting point: 127°–128° C.
Elemental Analysis for $C_{24}H_{44}O_6$:
Found: C, 67.39%; H, 10.59%
Calcd: C, 67.26%; H, 10.35%
NMR: 0.85 (3H, m), 1.26 (32H, m), 3.51 (2H, m), 3.91 (3H, m), 4.75 (1H, d, 1 Hz)

The physical properties of 2-O-octadecyl-L-ascorbic acid in the following examples were the same as those illustrated above.

EXAMPLE 2

Potassium t-butoxide (1 g, 9 mmol) was added to isopropyl alcohol (30 ml) in a stream of nitrogen and dissolved therein. 5,6-O,O-Isopropylidene-L-ascorbic acid (1.1 g, 5 mmol) was added to the solution and dissolved by heating. Then, octadecyl benzenesulfonate (2.5 g, 6 mmol) was added to the solution and stirred at about 60° C. for 2 hours. 2 N Hydrochloric acid (10 ml) was added to the reaction mixture and stirred under reflux for one hour. After cooling, methylene chloride (30 ml) and water (30 ml) were added to the reaction mixture and phases were separated. The aqueous phase was extracted with methylene chloride (30 ml). The extract was combined with the organic phase, dried over anhydrous magnesium sulfate and concentrated under reduced pressure. The crude crystals obtained were recrystallized from ethyl acetate to obtain 0.96 g of 2-O-octadecyl-L-ascorbic acid (yield: 44.8%).

EXAMPLE 3

Potassium t-butoxide (1 g, 9 mmol) was added to t-butyl alcohol (30 ml) in a stream of nitrogen and dissolved therein. 5,6-O,O-Isopropylidene-L-ascorbic acid (1.1 g, 5 mmol) was added to the solution and dissolved by heating. Then, octadecyl benzenesulfonate (2.5 g, 6 mmol) was added to the solution and stirred at about 60° C. for 2 hours. 2 N Hydrochloric acid (10 ml) was added to the reaction mixture and stirred under reflux for one hour. After cooling, methylene chloride (30 ml) and water (30 ml) were added to the reaction mixture and phases were separated. The aqueous phase was extracted with methylene chloride (30 ml). The extract was combined with the organic phase, dried over anhydrous magnesium sulfate and concentrated under reduced pressure. The crude crystals obtained were recrystallized from ethyl acetate to give 0.56 g of 2-O-octadecyl-L-ascorbic acid (yield: 26.1%).

EXAMPLE 4

Potassium t-butoxide (1 g, 9 mmol) was added to ethyl alcohol (30 ml) in a stream of nitrogen and dissolved therein. 5,6-O,O-Isopropylidene-L-ascorbic acid (1.1 g, 5 mmol) was added to the solution and dissolved by heating. Then, octadecyl benzenesulfonate (2.05 g, 5 mmol) was added and stirred at about 60° C. for 2 hours. 2 N Hydrochloric acid (10 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and concentrated under reduced pressure. The crude crystals obtained were recrystallized from ethyl acetate to obtain 0.77 g of 2-O-octadecyl-L-ascorbic acid (yield: 35.9%).

EXAMPLE 5

Sodium hydride (0.5 g, 60% in oil, 10 mmol) was added to methanol (15 ml) in a stream of nitrogen and dissolved therein. 5,6-O,O-Isopropylidene-L-ascorbic acid (1.1 g, 5 mmol) was added to the solution and dissolved with heating. Then, octadecyl benzenesulfonate (2.05 g, 5 mmol) was added to the solution and stirred at about 60° C. for 2 hours. 2 N Hydrochloric acid (10 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by high performance liquid chromatography (HPLC) to confirm that 1.08 g of 2-O-octadecyl-L-ascorbic acid (yield: 50.2 %) was contained.

Conditions for HPLC
Column: Unisil QC8 5 μm, 4×150 mm
Mobile phase: 0.02 M $KH_2PO_4$ containing 0.001% $Na_2S_2O_3$: $CH_3CN$=35: 65, pH 3

EXAMPLE 6

Sodium hydroxide (0.45 g, 11 mmol) was added to a mixture of methanol (15 ml) and water (0.5 ml) in a stream of nitrogen and dissolved therein. 5,6-O,O-Isopropylidene-L-ascorbic acid (1.1 g, 5 mmol) was added to the solution and dissolved by heating. Then, octadecyl benzenesulfonate (2.05 g, 5 mmol) was added to the solution and stirred at about 60° C. for 2 hours. 2 N Hydrochloric acid (10 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by HPLC under the same conditions as described in Example 5 to obtain 0.87 g of 2-O-octadecyl-L-ascorbic acid (yield: 40.6%).

EXAMPLE 7

Sodium hydride (0.4 g, 60% in oil, 10 mmol) was added to ethyl alcohol (30 ml) in a stream of nitrogen and dissolved therein. 5,6-O,O-Isopropylidene-L-ascorbic acid (1.1 g, 5 mmol) was added to the solution and dissolved by heating. Then, octadecyl benzenesulfonate (2.05 g, 5 mmol) was added to the solution and stirred at about 60° C. for 2 hours. 2 N Hydrochloric acid (10 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by HPLC under the same conditions as described in Example 5 to confirm that 1.01 g of 2-O-octadecyl-L-ascorbic acid (yield: 46.9%) was contained.

EXAMPLE 8

5,6-O,O-Isopropylidene-L-ascorbic acid (1.1 g, 5 mmol) was added to a mixture of methanol (15 ml) and sodium methoxide (2 g, 28% (w/w) methanol solution, 10 mmol) in a stream of nitrogen and dissolved by heating. Then, octadecyl benzenesulfonate (2.05 g, 5 mmol) was added to the solution and stirred at about 60° C. for 2 hours. After cooling, water (30 ml) was added to the reaction mixture and it was extracted with methylene chloride (30 ml). The organic extract was dried over anhydrous magnesium sulfate and concentrated under reduced pressure. The crude crystals obtained were recrystallized from isopropyl ether to obtain 1.22 g of 5,6-O,O-isopropylidene-2-O-octadecyl-L-ascorbic acid (yield: 52%).

Melting point: 81°–82° C.

NMR: 0.86 (3H, m), 1.25 (32H, m), 1.36 (3H, s), 1.41 (3H, s), 3.80–4.30 (5H, m), 4.68 (1H, d, 1 Hz)

EXAMPLE 9

5,6-O,O-Isopropylidene-L-ascorbic acid (1.1 g, 5 mmol) was added to a mixture of methanol (15 ml) and sodium methoxide (2 g, 28% (w/w) methanol solution, 10 mmol) in a stream of nitrogen and dissolved therein. Then, 1-iodooctadecane (1.9 g, 5 mmol) was added to the solution and the mixture was stirred at 60° C. for 2 hours. 2 N Hydrochloric acid (5 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by HPLC to confirm that 0.6 g of 2-O-octadecyl-L-ascorbic acid (yield: 28.0%) was contained.

EXAMPLE 10

5,6-O,O-Isopropylidene-L-ascorbic acid (1.1 g, 5 mmol) was added to a mixture of methanol (15 ml) and sodium methoxide (2 g, 28% (w/w) methanol solution, 10 mmol) in a stream of nitrogen and dissolved therein. Then, 1-bromooctadecane (1.7 g, 5 mmol) was added to the solution and the mixture was stirred at 60° C. for 2 hours. 2 N Hydrochloric acid (5 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by HPLC to confirm that 0.46 g of 2-O-octadecyl-L-ascorbic acid (yield: 21.6%) was contained.

EXAMPLE 11

5,6-O,O-Isopropylidene-L-ascorbic acid (1.1 g, 5 mmol) was added to a mixture of methanol (15 ml) and sodium methoxide (2 g, 28% (w/w) methanol solution, 10 mmol) in a stream of nitrogen and dissolved therein. Then, octadecyl p-chlorobenzenesulfonate (2.23 g, 5 mmol) was added to the solution and the mixture was stirred at 60° C. for one hour. 2 N Hydrochloric acid (5 ml) was added to the reaction mixture and stirred under reflux for one hour. After cooling, methylene chloride (30 ml), ethyl acetate (30 ml) and water (30 ml) were added to the reaction mixture and phases were separated. The aqueous phase was extracted with methylene chloride (30 ml). The extract was combined with the organic phase, dried over anhydrous magnesium sulfate and determined by HPLC to confirm that 0.94 g of 2-O-octadecyl-L-ascorbic acid (yield: 43.9%) was contained.

EXAMPLE 12

5,6-O,O-Isopropylidene-L-ascorbic acid (579 g, 2.68 mol) was added to a mixture of methanol (6 liters) and sodium methoxide (1,034 g, 28% (w/w) methanol solution, 5.36 mol) in a stream of nitrogen and dissolved therein. Then, tetradecyl benzene-sulfonate (1,015 g, 2.86 mol) was added to the solution and the mixture was stirred at 50° to 60° C. for about 3 hours. 2 N Hydrochloric acid (2.9 liters) was added to the reaction mixture and stirred under reflux for one hour. Water (8 liters) was added thereto and cooled to 20° C. or lower. The crystals precipitated were collected by filtration, dried and recrystallized from ethyl acetate to obtain 315 g of 2-O-tetradecyl-L-ascorbic acid (yield: 31.6%).

Melting point: 125°–126° C.

Elemental Analysis for $C_{20}H_{36}O_6$:

Found: C, 64.30%; H, 9.92%

Calcd: C, 64.49%; H, 9.74%

NMR: 0.85 (3H, m), 1.25 (24H, m), 3.51 (2H, m), 3.90 (3H, m), 4.74 (1H, d, 1 Hz)

EXAMPLE 13

5,6-O,O-Isopropylidene-L-ascorbic acid (560 g, 2.59 mol) was added to a mixture of methanol (8.4 liters) and sodium methoxide (999 g, 28% (w/w) methanol solution, 5.18 mol) in a stream of nitrogen and dissolved therein. Then, pentadecyl benzenesulfonate (954.6 g, 2.59 mol) was added to the solution and the mixture was stirred at 50° to 60° C. for 2.5 hours. 2 N Hydrochloric acid (2.8 liters) was added to the reaction mixture and stirred under reflux for one hour. Water (8 liters) was added thereto and cooled to 20° C. or lower. The crystals precipitated were collected by filtration, dried and recrystallized from ethyl acetate to obtain 409 g of 2-O-pentadecyl-L-ascorbic acid (yield: 40.8%).

Melting point: 125°–126° C.
Elemental Analysis for $C_{21}H_{38}O_6$:
Found: C, 65.33%; H, 10.01%
Calcd: C, 65.26%; H, 9.91%
NMR: 0.85 (3H, m), 1.26 (26H, m), 3.45 (2H, m), 3.86 (3H, m), 4.73 (1H, d, 1 Hz)

EXAMPLE 14

5,6-O,O-Isopropylidene-L-ascorbic acid (540 g, 2.50 mol) was added to a mixture of methanol (8.1 liters) and sodium methoxide (965 g, 28% (w/w) methanol solution, 5.00 mol) in a stream of nitrogen and dissolved therein. Then, hexadecyl benzenesulfonate (956.5 g, 2.50 mol) was added to the solution and the mixture was stirred at 50° to 60° C. for 2.5 hours. 2 N Hydrochloric acid (2.7 liters) was added to the reaction mixture and stirred under reflux for one hour. Water (8.1 liters) was added thereto and cooled to 20° C. or lower. The crystals precipitated were collected by filtration, dried and recrystallized from ethyl acetate to obtain 400 g of 2-O-hexadecyl-L-ascorbic acid (yield: 40.0%).

Melting point: 125°–126° C.
Elemental Analysis for $C_{22}H_{40}O_6$:
Found: C, 66.07%; H, 10.23%
Calcd: C, 65.97%; H, 10.07%
NMR: 0.86 (3H, m), 1.24 (28H, m), 3.59 (2H, m), 3.94 (3H, m), 4.75 (1H, d, 1 Hz)

EXAMPLE 15

5,6-O,O-Isopropylidene-L-ascorbic acid (2.16 g, 10 mmol) was added to a mixture of methanol (30 ml) and sodium methoxide (4.0 g, 28% (w/w) methanol solution, 20 mmol) in a stream of nitrogen and dissolved therein. Then, heptadecyl benzenesulfonate (4.0 g, 10 mmol) was added to the solution and the mixture was stirred at 60° C. for 2 hours. 2 N Hydrochloric acid (10 ml) was added to the reaction mixture and stirred under reflux for one hour. Water (30 ml) was added thereto and cooled to 20° C. or lower. The crystals precipitated were collected by filtration, dried and recrystallized from ethyl acetate to obtain 1.52 g of 2-O-heptadecyl-L-ascorbic acid (yield: 36.7%).

Melting point: 127°–129° C.
Elemental Analysis for $C_{23}H_{42}O_6$:
Found: C, 66.58%; H, 10.35%
Calcd: C, 66.63%; H, 10.21%
NMR: 0.86 (3H, m), 1.27 (30H, m), 3.54 (2H, m), 3.86 (3H, m), 4.75 (1H, d, 1 Hz)

EXAMPLE 16

5,6-O,O-Isopropylidene-L-ascorbic acid (2.16 g, 10 mmol) was added to a mixture of methanol (30 ml) and sodium methoxide (4.0 g, 28% (w/w) methanol solution, 20 mmol) in a stream of nitrogen and dissolved therein. Then, icosyl benzenesulfonate (4.4 g, 10 mmol) was added to the solution and the mixture was stirred at 60° C. for 2 hours. 2 N Hydrochloric acid (10 ml) was added to the reaction mixture and stirred under reflux for one hour. Water (30 ml) was added thereto and the mixture was cooled to 20° C. or lower. The crystals precipitated were collected by filtration, dried and recrystallized from ethyl acetate to give 1.86 g of 2-O-icosyl-L-ascorbic acid (yield: 40.7%).

Melting point: 126°–128° C.
Elemental Analysis for $C_{26}H_{48}O_6$:
Found: C, 68.61%; H, 10.72%
Calcd: C, 68.38%; H, 10.59%
NMR: 0.85 (3H, m), 1.23 (36H, m), 3.45 (2H, m), 3.86 (3H, m), 4.70 (1H, d, 1 Hz)

EXAMPLE 17

5,6-O,O-Isopropylidene-L-ascorbic acid (112.4 g, 0.52 mol) was added to a mixture of methanol (1.5 liters) and sodium methoxide (200 g, 28% (w/w) methanol solution, 1.04 mol) in a stream of nitrogen and dissolved therein. Then, dodecyl benzenesulfonate (170 g, 0.52 mol) was added to the solution and the mixture was stirred at 56° to 60° C. for 2 hours. 2 N Hydrochloric acid (0.5 liter) was added to the reaction mixture and stirred under reflux for one hour. The reaction mixture was concentrated to about one-third of its initial volume. Water (0.3 liter) was added to the concentrate and extracted with ethyl acetate (0.5 liter × 3). The extract was dried over anhydrous magnesium sulfate and concentrated under reduced pressure. The concentrated residue was recrystallized from ethyl acetate to obtain 40.0 g of 2-O-dodecyl-L-ascorbic acid (yield: 22.3%).

Melting point: 124°–125° C.
Elemental Analysis for $C_{18}H_{32}O_6$:
Found: C, 62.67%; H, 9.35%
Calcd: C, 62.77%; H, 9.34%
NMR: 0.85 (3H, m), 1.24 (20H, m), 3.43 (2H, m), 3.85 (3H, m), 4.73 (1H, d, 1 Hz)

EXAMPLE 18

5,6-O,O-Isopropylidene-L-ascorbic acid (2.2 g, 10 mmol) was added to a mixture of methanol (30 ml) and sodium methoxide (4.0 g, 28% (w/w) methanol solution, 20 mmol) in a stream of nitrogen and dissolved therein. Then, (3-phenyl)propyl benzenesulfonate (2.7 g, 10 mmol) was added to the solution and the mixture was stirred at 60° C. for 2 hours. 2 N Hydrochloric acid (12 ml) was added to the reaction mixture and stirred under reflux for one hour. The reaction mixture was concentrated under reduced pressure. Water (50 ml) was added to the residue and extracted with ethyl acetate (50 ml × 2). The extract was concentrated under reduced pressure and the resulting crude product was subjected to chromatography on silica gel (100 g) (developing solvent: ethyl acetate-n-hexane (1:1)) and further recrystallized from ethyl acetate-isopropyl ether (1:1) to obtain 0.88 g of 2-O-(3-phenyl)propyl-L-ascorbic acid (yield: 29.9%).

Melting point: 107°–108° C.
Elemental Analysis for $C_{15}H_{18}O_6$:
Found: C, 61.07%; H, 6.14%
Calcd C, 61.22%; H, 6.16%
NMR: 1.92 (2H, m), 2.67 (2H, m), 3.48 (2H, m), 3.83 (1H, m), 3.92 (2H, t, 7 Hz), 4.77 (1H, d, 3 Hz)

EXAMPLE 19

5,6-O,O-Isopropylidene-L-ascorbic acid (1.1 g, 10 mmol) was added to a mixture of methanol (15 ml) and sodium methoxide (2.0 g, 28% (w/w) methanol solution, 10 mol) in a stream of nitrogen and dissolved therein. Then, (2-octadecyl)ethyl benzenesulfonate (2.3 g, 5 mmol) was added to the solution and the mixture was stirred at 60° C. for 2 hours. 2 N Hydrochloric acid (5 ml) was added to the reaction mixture and stirred under reflux for one hour. The reaction mixture was concentrated under reduced pressure. Water (50 ml) was added to the residue and extracted with ethyl acetate (100 ml×2). The extract was concentrated under reduced pressure and the resulting crude product was recrystallized from ethyl acetate and further from ethanol to obtain 0.68 g of 2-O-(octadecyloxy)ethyl-L-ascorbic acid (yield: 27%).

Melting point: 81°–82° C.
Elemental Analysis for $C_{26}H_{48}O_7$:
Found: C, 65.79%; H, 10.50%
Calcd: C, 66.07%; H, 10.24%
NMR: 0.85 (3H, m), 1.26 (32H, m), 3.06–3.85 (10H, m), 3.95 (2H, m), 4.74 (1H, d, 1.3 Hz)

Reference Example 1

5,6-Isopropylidene-3-O-ethoxymethyl-L-ascorbic acid (6.7 g, 24 mmol) was added to N,N-dimethylformamide (90 ml) and dissolved therein. Octadecyl benzenesulfonate (12.1 g, 29 mmol) and potassium carbonate (6.8 g, 48 mmol) were added to the solution and stirred at about 45° C. for 3 hours. The reaction mixture was cooled to room temperature, water (150 ml) was added thereto, and the pH was adjusted to 7.5 with 2 N hydrochloric acid. The mixture was extracted with ethyl acetate (140 ml×2), and the organic phase was dried over anhydrous sodium sulfate and concentrated under reduced pressure to obtain 17.6 g of 5,6-isopropylidene-3-O-ethoxymethyl-2-O-octadecyl-L-ascorbic acid as an oil. The oil was dissolved in ethyl alcohol (28 ml), 1 N hydrochloric acid (9.4 ml) was added thereto and the mixture was refluxed for about one hour. The reaction mixture was concentrated under reduced pressure, ethyl acetate (80 ml) was added to the residue and the mixture was heated to obtain a solution. The solution was cooled and stirred at about 10° C. for one hour. The crystals precipitated were collected by filtration and recrystallized from a mixed solvent of toluene (90 ml) and ethyl acetate (22 ml) to obtain 4.86 g of 2-O-octadecyl-L-ascorbic acid (yield: 46.2%).

Melting point: 127°–128° C.
NMR: 0.85 (3H, m), 1.26 (32H, m), 3.51 (2H, m), 3.91 (3H, m), 4.75 (1H, d, 1 Hz)

Reference Example 2

5,6-Isopropylidene-3-O-ethoxymethyl-L-ascorbic acid (1.37 g, 5 mmol) was added to methanol (15 ml) and dissolved therein. Octadecyl benzenesulfonate (2.05 g, 5 mmol) and sodium methoxide (1 g, 28 % (w/w) methanol solution, 5 mmol) were added to the solution and stirred at about 50° C. for 2 hours. The reaction mixture was cooled to room temperature, water (30 ml) was added thereto and the pH was adjusted to 7.5 with 2 N hydrochloric acid. The mixture was extracted with ethyl acetate (25 ml×2), and the organic phase was dried over anhydrous sodium sulfate and concentrated under reduced pressure to obtain 3.6 g of 5,6-isopropylidene-3-ethyoxymethyl-2-O-octadecyl-L-ascorbic acid as an oil. The oil was dissolved in ethyl alcohol (10 ml), 1 N hydrochloric acid (1.8 ml) was added thereto and the mixture was refluxed for about one hour. The reaction mixture was concentrated under reduced pressure, and ethyl acetate (10 ml) was added to the residue. The mixture was heated to obtain a solution and it was cooled and stirred at about 10° C. for one hour. The crystals precipitated were collected by filtration, and they were recrystallized from a mixed solvent of toluene (8 ml) and ethyl acetate (2 ml) to obtain 0.86 g of 2-O-octadecyl-L-ascorbic acid (yield: 40.2%).

As described hereinabove, according to the present invention, the hydroxy group at the 2-position of ascorbic acid can be subjected to a substitution reaction without protecting the hydroxy group at the 3-position. Therefore, from the industrial point of view, the process of the present invention is economically and operationally advantageous because it involves less reaction steps. Further, in the substitution reaction of the hydroxy group at the 2-position, there is less possibility that the process of the present invention is accompanied by the side reaction wherein the hydroxy group at the 3-position is partly substituted. Therefore, ascorbic acid derivatives wherein the hydroxy group at the 2-position is substituted can be advantageously produced on an industrial scale.

What is claimed is:

1. A process for producing a compound of the formula (IV):

where $R^o$ is hydrogen, alkyl having 1 to 6 carbon atoms, phenyl, a group of the formula

or a group of the formula

(wherein X an acetal or ketal group); and $R^1$ is an alkyl or alkenyl group having up to 22 carbon atoms which may be substituted with phenyl or alkoxy having 1 to 22 carbon atoms, which comprises reacting a compound of the formula (I):

wherein $R^o$ is as defined above, with a compound of the formula (II):

wherein R¹ is as described above; and Y is halogen or optionally substituted sulfonyloxy, in the presence of a compound of the formula (III):

RO—Z  (III)

wherein R is hydrogen, or primary, secondary or tertiary alkyl having 1 to 10 carbon atoms; and Z is an alkali metal or an alkaline earth metal.

2. A process according to claim 1, wherein the reaction is carried out in the presence of a primary, secondary or tertiary alcohol.

3. A process according to claim 1, wherein the reaction is carried out in the presence of an inert gas.

4. A process according to claim 1, wherein the reaction is carried out at a temperature of from 10° C. to the boiling point of a solvent used.

5. A process according to claim 4, wherein the reaction is carried out at 40° to 80° C. for 1 to 4 hours.

6. A process according to claim 1, wherein the compound of the formula (II) is used in an amount of 0.5 to 3.0 molar equivalent based on the compound of the formula (I).

7. A process according to claim 1, wherein the compound of the formula (III) is used in an amount of 1.5 to 3.0 molar equivalent based on the compound of the formula (I).

8. A process according to claim 1 which further comprises hydrolyzing the compound of formula (IV) to produce the compound of formula (V):

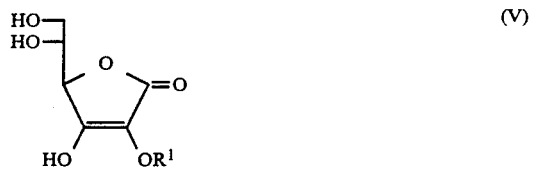

wherein R¹ is as defined in claim 1.

9. A process according to claim 8, wherein an acidic hydrolysis is carried out.

10. A process according to claim 9, wherein the hydrolysis is carried out at 10° to 80° C. for 1 to 2 hours.

* * * * *